United States Patent [19]

Oppelt

[11] Patent Number: 4,761,803
[45] Date of Patent: Aug. 2, 1988

[54] X-RAY DIAGNOSTICS INSTALLATION

[75] Inventor: Sylvester Oppelt, Bamberg, Fed. Rep. of Germany

[73] Assignee: Siemens Aktiengesellschaft, Berlin and Munich, Fed. Rep. of Germany

[21] Appl. No.: 52,271

[22] Filed: May 21, 1987

[30] Foreign Application Priority Data

Jun. 5, 1986 [DE] Fed. Rep. of Germany ....... 3618869

[51] Int. Cl.⁴ .............................................. H05G 1/64
[52] U.S. Cl. ...................................... 378/99; 358/111
[58] Field of Search ............................ 378/41, 92, 99; 358/111

[56] References Cited

U.S. PATENT DOCUMENTS

| 3,924,064 | 12/1975 | Nomura et al. | 378/99 |
| 4,149,082 | 4/1979 | Haendle et al. | 378/41 |
| 4,207,595 | 6/1980 | Dittrich et al. | 378/99 |
| 4,658,410 | 4/1987 | Haendle et al. | 378/41 |
| 4,674,107 | 6/1987 | Urban et al. | 378/99 |

FOREIGN PATENT DOCUMENTS

| 0168559 | 1/1986 | European Pat. Off. |
| 3006749 | 4/1981 | Fed. Rep. of Germany |
| 3122056 | 12/1982 | Fed. Rep. of Germany |
| 3220751 | 12/1983 | Fed. Rep. of Germany |

Primary Examiner—Craig E. Church
Assistant Examiner—John C. Freeman
Attorney, Agent, or Firm—Hill, Van Santen, Steadman & Simpson

[57] ABSTRACT

An x-ray diagnostics installation has two x-ray sources for generating two intersecting x-ray beams, at least one image converter for generating an image signal, and a monitor connected thereto. The image signal of a first image converter is supplied to an image computer which calculates the projection of one x-ray beam in the plane of the other x-ray beam. An addition stage is connected between a second image converter and the monitor, the addition stage mixing the output signal of the image computer and that of the second image converter.

3 Claims, 1 Drawing Sheet

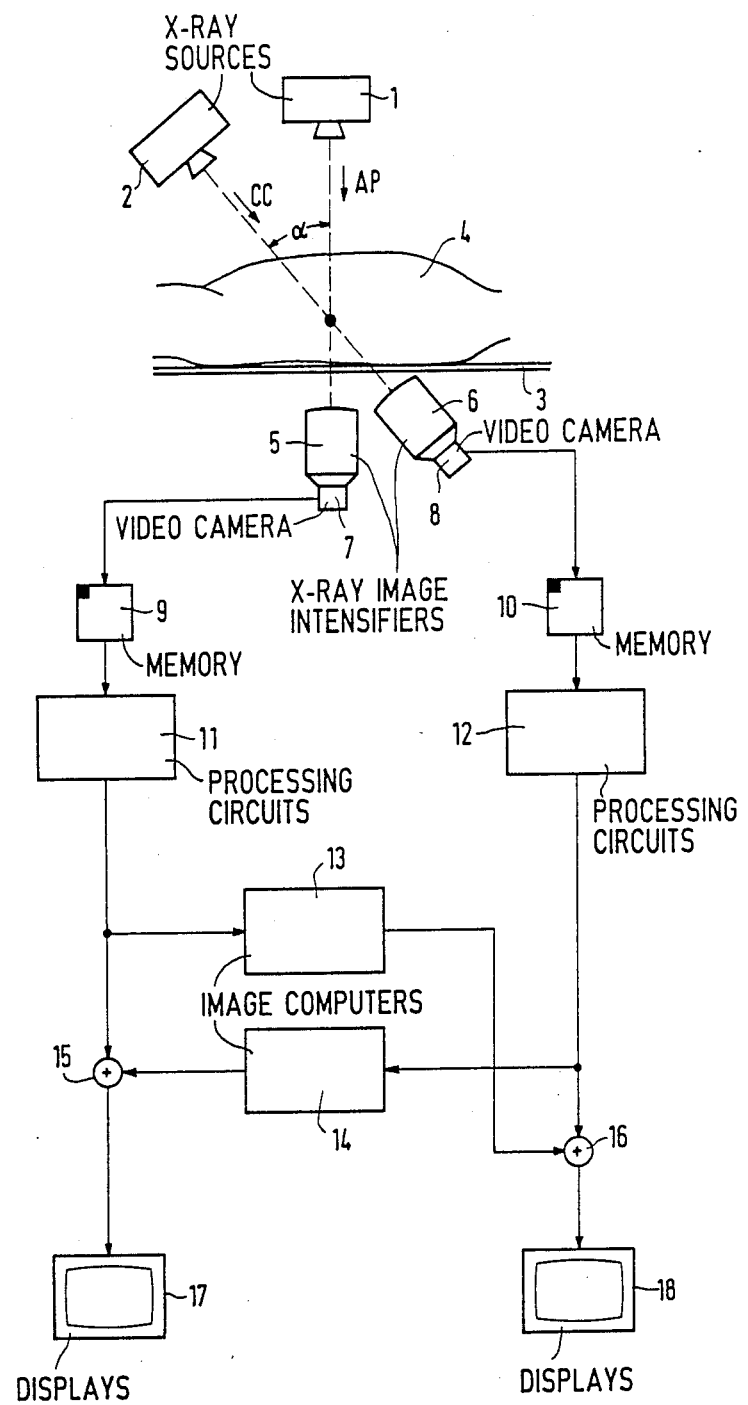

X-RAY DIAGNOSTICS INSTALLATION

BACKGROUND OF THE INVENTION

1. Field of the Invention

The invention is directed to an x-ray diagnostics installation of the type having two x-ray sources for generating two intersecting x-ray beams, at least one image converter for genrating an image signal, and a monitor connected thereto. Such installations serve for precise locating of body parts in x-ray stereo systems or two-plane systems.

2. Description of the Prior Art

German OS No. 31 32 056 discloses such an apparatus which, for example, serves the purpose of locating urinary calculi, kidney stones, gallstones or the like in an apparatus for the in situ disintegration of such calculi in the body of a life form with a shock wave generator. In a focussing chamber of the shockwave generator, a shock wave generated, for example, by spark discharge, is concentrated on the calculus and comminutes it. For the precise locating of the calculus and alignment thereof in the focus of the focussing chamber, the apparatus is connected to an x-ray examination installation. In radioscopy operation, the individual images of a pair of stereo images are rolled into the image storage either individually or integrated over a plurality of images in the video clock. A problem results in that the calculi, particularly if they are small, show only a slight degree of contrast, and are thus difficult to recognize.

SUMMARY OF THE INVENTION

It is an object of the present invention to provide an x-ray diagnostics installation of the type initially described wherein a good identification of small parts with low contrast scope is established.

This object is achieved in an x-ray installation constructed in accordance with the principles of the present invention wherein the picture signal of a first image converter is supplied to a picture computer which calculates the projection of the one x-ray beam in the plane of the other x-ray beam, and having an addition stage connected between a second image converter and the monitor. The addition stage mixes the respective output signals of the image computer and the second image converter. The visibility of the small calculi is thereby enhanced.

A calculation reproducable on two monitors can ensue when an addition stage and an image computer are respectively connected to each of the two image converters forming two output chains, the respective outputs of the image computers being respectively connected to the addition stage in the other chain.

DESCRIPTION OF THE DRAWINGS

The single FIGURE is a schematic block diagram of an xray diagnostics installation constructed in accordance with the principles of the present invention.

DESCRIPTION OF THE PREFERRED EMBODIMENTS

The FIGURE shows an x-ray diagnostics installation comprising two x-ray tubes 1 and 2 which generate x-ray beams which penetrate a patient 4 situated on a patient support 3, and which are incident on the input luminesce screens of x-ray image intensifiers 5 and 6. The x-ray tube 1 and the x-ray image intensifier 6 can be arranged such that the central ray of the x-ray beam of the x-ray tube 1 is perpendicularly incident on the patient 4 (a.p. projection). The x-ray tube 2 and the x-ray image intensifier 5, for example, are obliquely arranged such that the central ray of the x-ray tube 2 intersects the central ray of the x-ray tube 1 in a target area within the patient 4, for example, at an angle α of 45° (c.c. projection). As a result, radiographic images are obtained from two different projection directions, so that the patient 4 can be displaced by the patient support 3 such that, for example, a kidney stone is located in the target region of an apparatus for the disintegration of calculi.

The output signals of the video cameras 7 and 8 coupled to the x-ray image intensifier 5 and 6 are read into two image memories 9 and 10 which are part of two signal chains. The output signals of the image memories 9 and 10 are supplied to respective processing circuits 11 and 12 which, for example, filter the signals. The outputs of the processing circuit 11 and 12 are respectively connected to image computers 13 and 14 and also to the respective first inputs of addition stages 15 and 16. The respective outputs of the image computers 13 and 14 are connected to the second input of the addition stages 15 or 16 in the other signal chain. Monitors 17 and 18 are respectively connected to each of the addition stages 15 and 16.

After radioscopy has been carried out by the x-ray tubes 1 and 2, the x-ray pictures are converted into image signals by the image converters, the image intensifiers 5 and 6 and video cameras 7 and 8. These image signals are rolled into the image storages 9 and 10. These stored image signals are supplied to the respective image computers 13 and 14. By turning the a.p. projection image by the angle −α, the first image computer 13 uses the image signal corresponding to an a.p. projection to calculate an image signal corresponding to a c.c. projection. As the calculated image signal of a c.c. projection, this output signal of the first image computer 13 is supplied to the addition stage 16 and is mixed with the image signal of the c.c. projection contained in the first image storage 10 and is reproduced on the monitor 18.

In the same way, the output signal of the second image stored 12 which corresponds to a c.c. projection is converted into an a.p. projection image in the second image computer 14 by turning the c.c. projection image by the angle α. This calculated a.p. projection image is mixed with the a.p. projection stored in the image storage 9, in the addition stage 15, and is reproduced on the monitoring 17. Two separately identified video signals are thereby mixed, so that the contrast of the subject to be examined, for example the calculi, is enhanced. As a result, these calculi can still be recognized even when they have already been comminuted by a plurality of shock waves.

The mixing of the stored and the calculated signals in the addition stages 15 and 16 can, for example, ensue on the basis of mean value formation, i.e. addition and subsequent division by two. As a result, noise is particularly reduced, so that the recognizability is enhanced. For even more enhancement, an adjustable window region can subsequently blanked out from the sum signal, this then being reproduced on the monitor 17 and 18. Although modifications and changes may be suggested by those skilled in the art it is the intention of the inventor to embody within the patent warranted hereon all changes and modifications as reasonably and properly come within the scope of his contribution to the art.

I claim as my invention:

1. An x-ray diagnostics installation comprising:
    two x-ray sources respectively generating an x-ray beam in different planes, said x-ray sources being disposed such that said x-ray beams intersect in an examination subject;
    a first image converter means for generating an image signal from one of said x-ray beams of at least a portion of said examination subject;
    an image computer connected to said first image converter which calculates the projection of the x-ray beam incident on said first image converter in the plane of the other x-ray beam;
    a second image converter for generating an image signal corresponding to at least a portion of said examination subject;
    an addition stage having inputs connected to said image computer and said second image converter which adds the signals at said inputs; and
    means connected to the output of said addition stage for displaying a visual image of said portion of said examination subject.

2. An x-ray diagnostics installation as claimed in claim 1, further comprising:
    a further image computer connected to said second image converter;
    a further addition stage having inputs connected to said further image computer and said first image converter which adds the signals at said inputs; and
    means connected to the output of said further addition stage for generating a visual image of said portion of said examination subject.

3. An x-ray diagnostics installation comprising:
    a first x-ray source which generates an x-ray beam in a first plane directed at an examination subject;
    a second source which generates an x-ray beam in a second plane, different from said first plane, directed at said examination subject, said first and second x-ray sources being disposed such that said first and second planes intersect in said examination subject;
    a first image converter disposed for receiving said x-ray beam in said first plane attenuated by said examination subject and generating a first image signal therefrom;
    a second image converter disposed for receiving said x-ray beam in said second plane attenuated by said examination subject and generating an image signal therefrom;
    a first image computer to which said image signal from said first image converter is supplied, said first image computer calculating the projection of said x-ray beam in said first plane in said second plane;
    a second image computer to which said image signal from said second image converter is supplied, said second image computer calculating the projection of said x-ray beam in said second plane in said first plane;
    a first addition stage having an input to which said image signal from said first image converter is supplied and another input to which the output of said second image computer is supplied, said addition stage adding the signals at said inputs thereof;
    a second addition stage having an input to which said image signal from said second image converter is supplied and another input connected to the output of said first image computer, said second addition stage adding the signals at said inputs thereof;
    means connected to the output of said first addition stage for displaying a visual image of said examination subject from the output of said first addition stage; and
    means connected to said second addition stage for generating a visual image of said examination subject from the output of said second addition stage.

* * * * *